United States Patent [19]
Pohribnij et al.

[11] Patent Number: 6,035,260
[45] Date of Patent: *Mar. 7, 2000

[54] WRIST STRAP INTEGRITY CHECK CIRCUITRY

[75] Inventors: Walter Jerry Pohribnij, Palatine; Warren E. Guthrie, Wheaton, both of Ill.

[73] Assignee: Northrop Grumman Corporation, Los Angeles, Calif.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/842,069

[22] Filed: Apr. 23, 1997

[51] Int. Cl.[7] .................................................. H05F 3/00
[52] U.S. Cl. ............................................. 702/58; 361/220
[58] Field of Search ...................... 702/58, 116; 324/500, 324/509, 510; 340/573, 649, 650; 361/212, 220

[56] References Cited

U.S. PATENT DOCUMENTS

| | | | |
|---|---|---|---|
| H330 | 9/1987 | Burich et al. | 324/500 |
| 4,155,116 | 5/1979 | Tawfik et al. | 364/119 |
| 4,509,531 | 4/1985 | Ward | 128/736 |
| 4,558,309 | 12/1985 | Antonevich | 340/649 |
| 4,598,275 | 7/1986 | Ross et al. | 340/573 |
| 4,638,399 | 1/1987 | Maroney et al. | 361/220 |
| 4,649,374 | 3/1987 | Hoigaard | 340/573 |
| 4,677,521 | 6/1987 | Frazier | 361/220 |
| 4,745,519 | 5/1988 | Breidegam | 361/220 |
| 4,800,374 | 1/1989 | Jacobson | 340/649 |
| 4,802,163 | 1/1989 | Hirabayashi | 371/15 |
| 4,858,125 | 8/1989 | Washizuka et al. | 364/413.01 |
| 4,952,928 | 8/1990 | Carroll et al. | 340/825.54 |
| 5,083,117 | 1/1992 | Hoigaard | 340/649 |
| 5,254,940 | 10/1993 | Oke et al. | 324/158 R |
| 5,337,290 | 8/1994 | Ventimiglia et al. | 368/10 |
| 5,430,735 | 7/1995 | Sauerwald et al. | 371/22.3 |
| 5,448,221 | 9/1995 | Weller | 340/539 |
| 5,515,858 | 5/1996 | Myllymaki | 128/670 |
| 5,650,945 | 7/1997 | Kita | 364/569 |
| 5,686,897 | 11/1997 | Loh | 340/649 |
| 5,745,037 | 4/1998 | Guthrie et al. | 340/573 |
| 5,872,455 | 2/1999 | Pohribnij et al. | 324/509 |

*Primary Examiner*—Melanie A. Kemper
*Attorney, Agent, or Firm*—Terry J. Anderson; Karl J. Hoch, Jr.

[57] ABSTRACT

Improved electronic circuitry incorporated into a tag attached to a user worn wrist strap of a static electrical discharge dissipation system. The electronic circuitry monitors the electrical connection of the wrist strap from the user to ground, and comprises a discharge resistor and a discharge resistor check circuit for monitoring the accuracy of the discharge resistor. The electronic circuitry further comprises a skin resistance check circuit for monitoring the electrical connection of the wrist strap to the user, and a ground fault detect circuit for monitoring the electrical connection of the wrist strap to ground.

29 Claims, 5 Drawing Sheets

FIG. 3A  HIGH LIMIT CHECK

FIG. 3B  LOW LIMIT CHECK

| OPERATION | SW1 | SW2 | SW3 | SW6 | SW7 | SW8 | SW10 |
|---|---|---|---|---|---|---|---|
| GND MONITOR | GND | GND | OC | OC | OC | INT | GND |
| DISCHARGE RESISTOR CHECK LOW LIMIT | GND | +V | COMP | OC | OC | GND | GND |
| DISCHARGE RESISTOR CHECK HIGH LIMIT | +V | GND | COMP | OC | OC | GND | GND |
| WRIST CHECK | OC | OC | +V | CL | CL | +V | OC |

FIG. 6

WRIST STRAP INTEGRITY CHECK CIRCUITRY

FIELD OF THE INVENTION

The present invention relates generally to static electrical charge dissipation devices, and more particularly to a static wrist strap which includes electronic circuitry adapted to monitor various sensors of the wrist strap and transmit the information back to a central location.

BACKGROUND OF THE INVENTION

For some time, the prior art has recognized the need to minimize static electrical charges in certain laboratory and manufacturing environments. The build-up of static electrical charges on sensitive items, including electronic components such as integrated circuit chips, may result in the catastrophic failure of such items. These highly sensitive items are particularly susceptible to damage from static electrical charges during manufacturing and assembly processes wherein the electrical leads of such items are typically exposed and unshielded. Once installed in the devices for which they are intended, such items are generally less susceptible to damage from static electrical charges, since they are substantially isolated therefrom and frequently grounded in a manner which prevents static electrical charge build-up.

In accordance with contemporary methodology, various means are utilized to mitigate the undesirable effects of static electrical charge build-up in the laboratory or manufacturing environment. For example, the manufacturing and assembly of static sensitive devices is typically conducted in an environmentally controlled facility which is adapted to minimize electrostatic charge build-up. Frequently, the humidity within the facility is maintained within a desirable range such that static charges tend to dissipate, through the moisture laden air, from the surfaces upon which such charges would otherwise accumulate. Additionally, it is also known to increase the ion content of the air within sensitive areas of such facilities so as to provide a means for neutralizing undesirable static electrical charges. The ions from the air combine with those of an opposite charge which define the undesirable static electrical charges, thus effecting the neutralization of such charges.

In addition to the foregoing, workers in the above-described facilities are generally required to utilize grounding straps upon one of their wrists and/or ankles, and are also often required to wear static charge dissipating clothing, e.g., gowns and/or other articles of clothing, so as to mitigate static charge build-up upon the person and/or their clothing. As used herein, the term wrist strap shall be defined to include such wrist straps, ankle straps, and/or other personnel grounding devices.

One such prior art wrist strap comprises a single line grounding strap which utilizes a single conductive line to bleed static electrical charges away from the user to ground. A resistor is preferably incorporated into the conductive line to ground so as to prevent a direct short to ground if the user should accidentally contact a hot or active electrical conductor. Thus, the inclusion of the resistor within the conductive line substantially enhances the safety of the wrist strap.

In these prior art wrist straps, it is known to continuously monitor the integrity of the conductive path to ground by monitoring the capacitance of the conductive line. In this respect, the capacitance of the conductive line is substantially reduced when the electrical connection of the wrist strap to the user is not adequate, i.e., an open or high resistance connection is present. The integrity of the conductive path may also be monitored in the prior art wrist straps by measuring continuity on an intermediate basis. However, such monitoring requires that the user periodically touch a ground so as to define a current loop through the conductive line, the user, and ground, through which continuity is measured. In the prior art wrist straps, the integrity of the conductive path is also monitored by monitoring the electrical connection of the wrist strap to ground.

To achieve the aforementioned functional attributes, prior art wrist straps are often provided with a capacitance circuit for monitoring the electrical connection of the wrist strap to the user by monitoring the capacitance of the conductive line. As previously indicated, the capacitance of the conductive line is dependent upon the presence of a user, as well as the integrity of the conductive line connection to the user via the wrist strap. In addition to the capacitance circuit, the prior art wrist straps are often provided with a resistance circuit which monitors the electrical connection of the wrist strap to ground, thus insuring the presence of an adequate ground to which electrical charges are bled from the user. With these prior art wrist bands, the user is typically alerted when electrical continuity through the wrist strap to ground is degraded. Thus, if any portion of the conductive path from the user to ground is not adequate to properly bleed off static electrical charge build-up upon the user, the user is alerted via a visual and/or audible alarm.

Though serving their intended purpose of bleeding static electrical charges from a user to ground, the prior art wrist bands possess certain deficiencies which detract from their overall utility. First, though such wrist bands include circuits for monitoring the electrical connections of the wrist band to the user and the conductive line to ground, they do not include a circuit for monitoring the discharge resistor which, as previously indicated, is often incorporated in the conductive line to enhance the safety of the wrist strap. Additionally, the circuitry incorporated in the prior art wrist straps is extremely complex, thus causing the size of the wrist straps to be extremely large. Additionally, the prior art circuitry necessitates increased power input which significantly reduces the life of the battery incorporated into the wrist strap.

SUMMARY OF THE INVENTION

The previously described deficiencies of the prior art wrist straps are overcome by the present invention. The present invention comprises a static wrist strap having an inexpensive radio transmitter (hereinafter referred to as a "tag") attached thereto or placed into electrical communication therewith. The tag includes electronic circuitry adapted to monitor various sensors and transmit the information back to a central location. The tag contains a microprocessor which determines when the sensors are to be checked and when the status of the sensors is to be transmitted to the central location. The unique circuitry of the present tag allows the same to conduct several different tests by multiplexing parts of the circuitry. Incorporated into the microprocessor of the present tag are two (2) comparators and additional circuitry which accomplish tasks that ordinarily take three (3) to four (4) comparators and some additional circuitry. The circuitry of the present tag also provides for the transmission of the monitored sensor information to the central location.

The unique electronic circuitry of the present tag monitors the ground connection for interrupts/failures to insure the integrity of the conductive path from the tag to ground. The electronic circuitry also monitors the skin resistance of the operator or user (which is preferably below 10 Megohms) to insure electrical connection between the electrodes of the tag (e.g., wrist strap) and the user's skin. To insure user safety, the discharge resister of the tag (which preferably has a value of 1 Megohm +/– 30%) is also monitored by the electronic circuitry, with such monitoring being accomplished in two (2) steps, i.e., by separately checking the high limit and the low limit of the discharge resister.

The uniqueness of the electronic circuitry incorporated into the tag is that it enables the microprocessor of the tag to conduct several tests without requiring the use of a larger microprocessor with more input/output pins and/or the use of more extensive external circuitry. The use of the smallest microprocessor possible and the rapid switching between tests allows for the minimization of the amount of power used by the microprocessor. This helps to maintain a reasonable battery life, using a relatively small battery. As such, the efficiency of the monitoring/test algorithms allows for the miniaturization of the tag, while still maintaining desired functionality.

More particularly, the present invention comprises electronic circuitry which is incorporated into the user worn tag of a static electrical discharge dissipation system wherein the tag is electrically connected to ground via a conductive line. The electronic circuitry of the present invention is adapted to monitor the electrical connection of the tag from the user to ground, and comprises a discharge resistor and a discharge resistor check circuit for monitoring the accuracy of the discharge resistor. In addition to the discharge resistor check circuit, the electronic circuitry comprises a skin resistance check circuit for monitoring the electrical connection of the tag to the user, and a ground fault detect circuit for monitoring the electrical connection of the tag to ground. The discharge resistor check circuit is itself configured to perform separate high and low limit checks of the discharge resistor. In the preferred embodiment, the discharge resistor check circuit, skin resistance check circuit, and ground fault detect circuit are each integrated into a sensor circuit of the electronic circuitry. The sensor circuit is itself incorporated into a microprocessor of the electronic circuitry, with the tag into which the electronic circuitry is incorporated preferably being integrated into or placed into electrical communication with a static wrist strap. However, those of ordinary skill in the art will recognize that the tag of the present invention may be used in conjunction with devices other than for wrist straps (e.g., ankle straps).

In the electronic circuitry of the present invention, the discharge resistor check circuit is configured to generate a discharge resistor signal, with the skin resistance check circuit being configured to generate a skin resistance signal. Similarly, the ground fault detect circuit is configured to generate a ground fault signal. The discharge resistor, skin resistance, and ground fault signals are transmitted to an interrogator unit via a transmission circuit which is preferably included in the electronic circuitry. The transmission circuit is itself configured to transmit the discharge resistor, skin resistance, and ground fault signals via a direct sequence spread spectrum having a data rate of approximately 33.33 kbps. Additionally, these signals are preferably transmitted by the transmission circuit to the interrogator unit at selected transmission cycles, and via a preferred carrier frequency of approximately 2414 Mhz +/– 1 Mhz. Each of the transmission cycles preferably comprises approximately five repetitions of the signals, with each repetition being separated by a random interval of approximately three seconds. Further, the transmission circuit is configured such that the transmission cycles preferably occur at random intervals of approximately five minutes. The transmission circuit is also configured to transmit the ground fault signal to the interrogator unit immediately upon the occurrence of an interrupt within the electrical connection of the tag to ground. The tag (e.g., wrist strap) into which the present electronic circuitry is incorporated will typically comprise a "transmit only" (TO) tag. However, those of ordinary skill in the art will recognize that the electronic circuitry may also be incorporated into a "transmit then receive" (TTR) tag as well.

In the preferred embodiment, the discharge resistor check circuit of the electronic circuitry is configured to periodically monitor the accuracy of the discharge resistor, with the skin resistance check circuit being configured to periodically monitor the electrical connection of the tag to the user. However, the ground fault detect circuit is configured to continuously monitor the electrical connection of the tag to ground.

The electronic circuitry of the present invention further comprises an alarm circuit for generating an audible alarm in response to certain conditions sensed by the electronic circuitry. In the preferred embodiment, the alarm circuit is configured to generate an audible alarm when the accuracy of the discharge resistor as monitored by the discharge resistor check circuit is outside the range of approximately 1 Megohm +/– 30%. The alarm circuit is also configured to generate an audible alarm when at least one, and preferably several, readings of the user's skin resistance as monitored by the skin resistance check circuit is above 10 Megohms, or when a ground fault condition is monitored by the ground fault detect circuit.

Further in accordance with the present invention, there is provided a method for monitoring the electrical connection of a user worn tag from the user to ground. The method comprises the initial step of providing electronic circuitry which is incorporated into the tag and includes a discharge resistor. The method further comprises the steps of monitoring the accuracy of the discharge resistor via a discharge resistor check circuit of the electronic circuitry, monitoring the electrical connection of the tag to the user via a skin resistance check circuit of the electronic circuitry, and monitoring the electrical connection of the tag to ground via a ground fault detect circuit of the electronic circuitry. The discharge resistor accuracy monitoring step is conducted by performing separate high and low limit checks of the discharge resistor.

The preferred method further comprises the step of transmitting a discharge resistor signal generated by the discharge resistor check circuit, a skin resistance signal generated by the skin resistance check circuit, and a ground fault signal generated by the ground fault detect circuit to an interrogator unit via a transmission circuit of the electronic circuitry. These signals are preferably transmitted from the transmission circuit to the interrogator unit at selected transmission cycles via a carrier frequency of approximately 2414 Mhz +/– 1 Mhz. The transmission cycles preferably occur at random intervals of approximately five minutes, with each of the transmission cycles preferably comprising approximately five repetitions of the signals, with each repetition being separated by a random interval of approximately three seconds.

The present method further comprises the step of generating an audible alarm in response to certain conditions of the electronic circuitry via an alarm circuit of the electronic circuitry. An audible alarm is generated when the accuracy of the discharge resistor as monitored by the alarm circuit is outside of the range of 1 Megohm +/− 30%. An audible alarm is also generated when at least one, and preferably several, readings of the user's skin resistance as monitored by the skin resistance check circuit is above 10 Megohms, or when a ground fault is monitored by the ground fault detect circuit.

BRIEF DESCRIPTION OF THE DRAWINGS

These, as well as other features of the present invention, will become more apparent upon reference to the drawings wherein.

DETAILED DESCRIPTION OF THE PREFERRED EMBODIMENT

Figure 1:
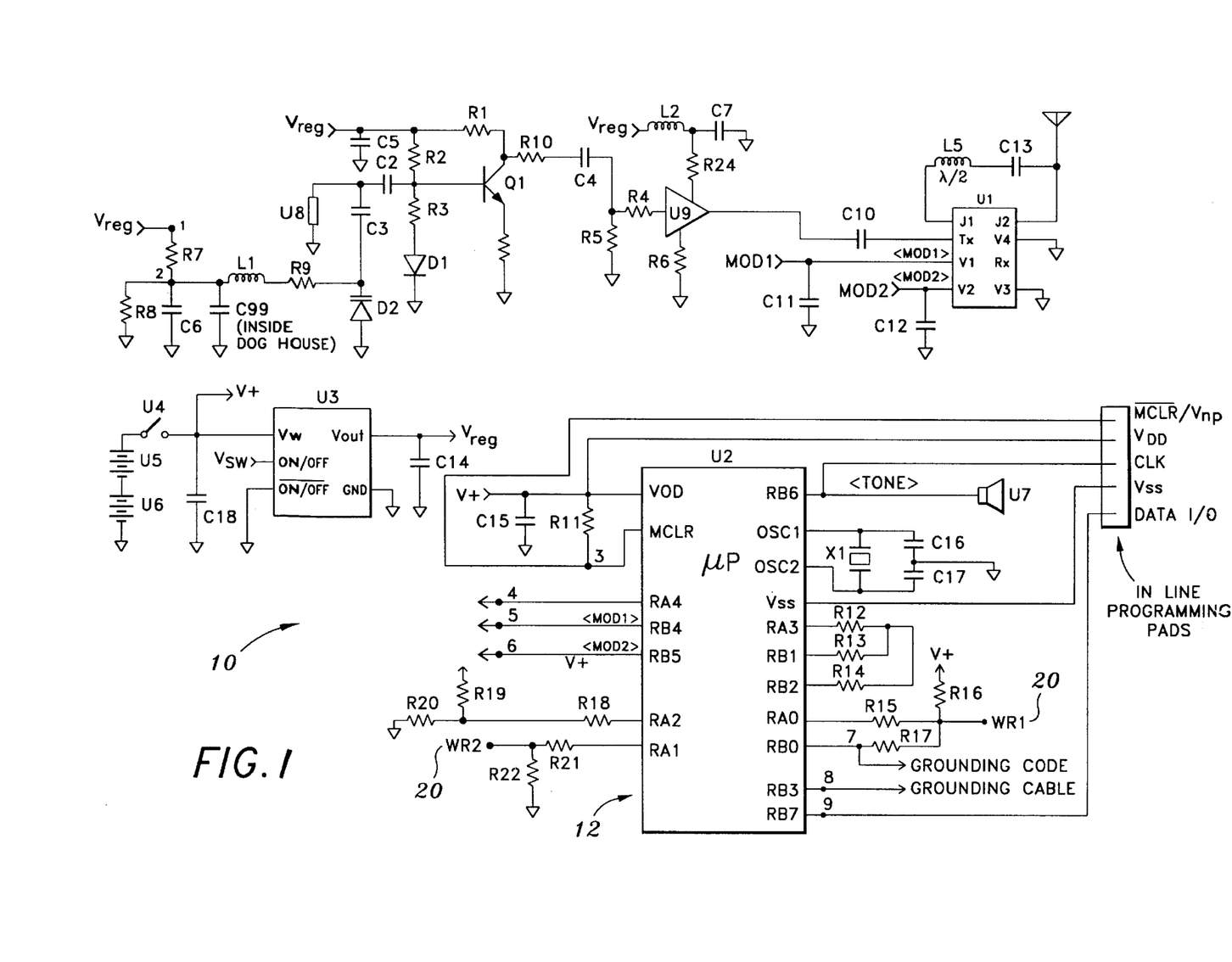
FIG. 1 is a complete electrical schematic of the tag constructed in accordance with the present invention.

Referring now to the drawings wherein the showings are for purposes of illustrating a preferred embodiment of the present invention only, and not for purposes of limiting the same, FIG. 1 schematically illustrates the complete electronic circuitry 10 constructed in accordance with the present invention. The electronic circuitry 10 is preferably incorporated into a "tag", and more particularly a "transmit only" (TO) tag. However, the electronic circuitry 10 may alternatively be incorporated into a "transmit then receive" (TTR) tag. The tag including the electronic circuitry 10 of the present invention is itself intended for use in conjunction with a selected radio frequency identification system protocol. As will be discussed in more detail below, TO tags including the electronic circuitry 10 are adapted to transmit a burst of direct sequence spread spectrum (DSSS) data at 33.33 kbps with random intervals. The data package consists of a tag identification and a status of various sensors. TTR tags including the electronic circuitry 10 are adapted to transmit a data package similar to tags, but are put into a receive mode following any transmissions. The receive mode facilitates the storage of data into the TTR tag memory for later extraction, initiating data retrieval, and initiating a variety of special functions.

As previously indicated, the electronic circuitry 10 of the present invention is preferably incorporated into a TO tag. The TO tag, which will hereinafter be referred to simply as the "tag", itself is preferably attached to or placed into electrical communication with an electrical discharge dissipation device such as a static wrist strap which is typically worn about the wrist of a user. In a preferred application, the wrist strap including the tag comprises part of a static electrical discharge dissipation system wherein the wrist strap is electrically connected to ground via a conductive line. In this respect, when the wrist strap is worn by the user, static electrical charges building up on the user's skin surface are bled to ground via the conductive line. Those of ordinary skill in the art will recognize that the tag may alternatively be attached to or placed into electrical communication with an ankle strap or a dissipation device which contacts another part of the user's body.

The electronic circuitry 10 of the tag is adapted to monitor various sensors and transmit the information back to a central location, and more particularly to an interrogator unit. The electronic circuitry 10 of the tag contains a microprocessor 12 which determines when the sensors of the tag are to be checked and when the status of the sensors is to be transmitted to the interrogator unit. The tag is adapted to conduct several different tests by multiplexing parts of the electronic circuitry 10. Incorporated into the microprocessor 12 are first and second comparators 14, 16, respectively, and additional circuitry which collectively accomplish tasks that ordinarily take three to four comparitors and some additional circuitry. The electronic circuitry 10 of the tag also provides for the transmission of the monitored sensor information to the interrogator unit.

As will also be described in more detail below, the electronic circuitry 10 monitors the ground connection of the wrist strap to ground for interrupts or failures to insure the integrity of the conductive path from the wrist strap to ground. The electronic circuitry 10 also monitors the skin resistance of the user to insure electrical connection between the electrodes of the wrist strap and the user's skin. Additionally, to insure user safety, the tag includes a discharge resistor, the accuracy of which is also monitored by the electronic circuitry 10 by separately checking the high and low limits thereof.

As previously explained, the uniqueness of the electronic circuitry 10 incorporated into the tag is that it enables the microprocessor 12 to conduct several tests without requiring the use of a larger microprocessor with more input/output pins and/or the use of more extensive external circuitry. The use of the smallest microprocessor possible and the rapid switching between tests allows for the minimization of the amount of power used by the microprocessor 12. This helps to maintain a reasonable battery life, using a relatively small battery. As such, the efficiency of the monitoring/test algorithms allows for the miniaturization of the tag, while still maintaining desired functionality.

Figure 2:
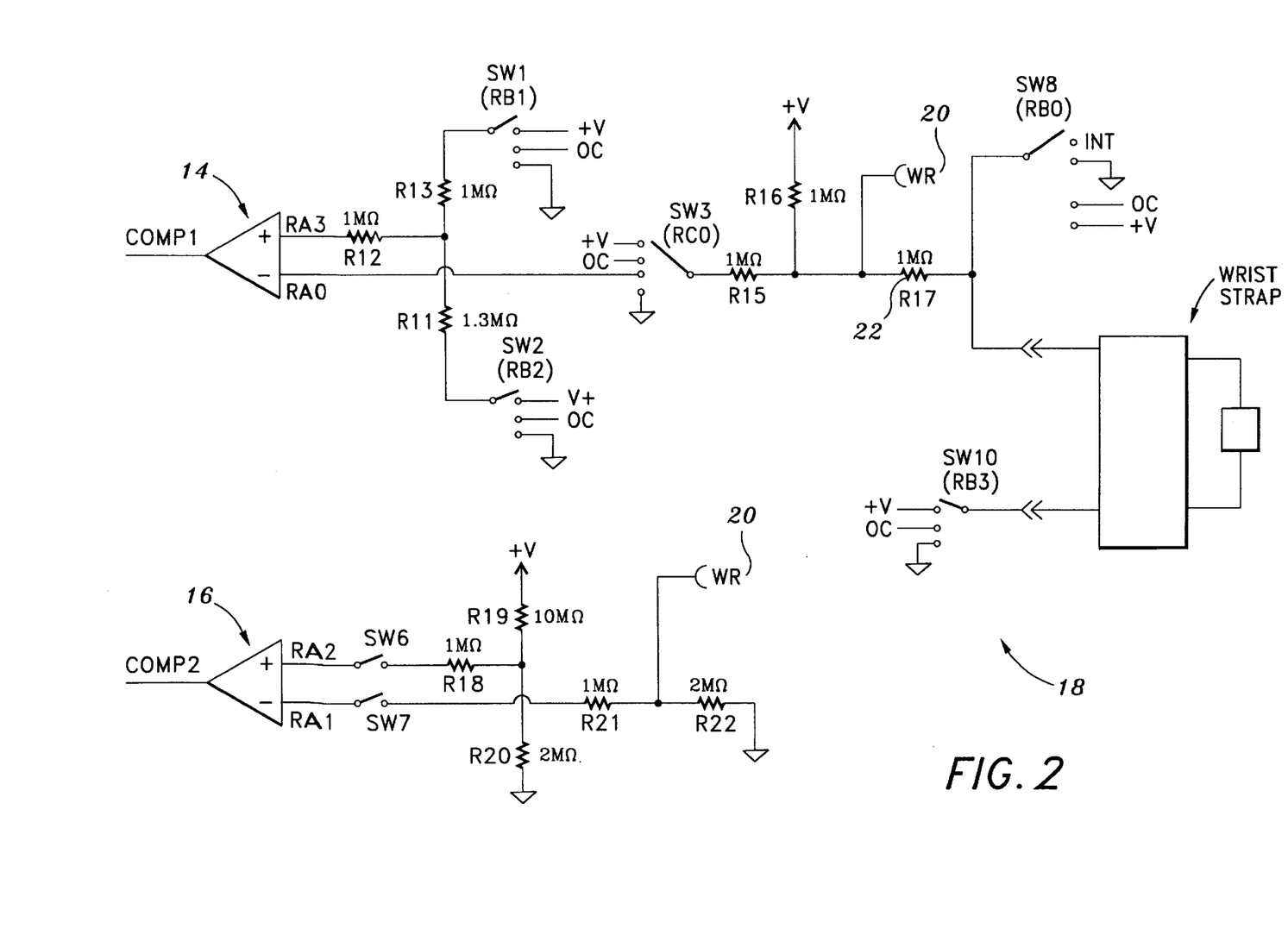
FIG. 2 is an electrical schematic of the sensor circuitry incorporated into the tag of the present invention.

Referring now to FIG. 2, schematically illustrated is a sensor circuit 18 of the electronic circuitry 10 which is internal to the microprocessor 12. The sensor circuit 18 includes the first comparator 14 and the second comparator 16, each of which are electrically connectible to a respective electrode 20 of the wrist strap. The electrodes 20 are intended to be placed into direct contact with the user's skin when the wrist strap is worn by the user. As previously indicated, the first and second comparators 14, 16, as well as all of the switches within the sensor circuit 18, are internal to the microprocessor 12, with all other components of the sensor circuit 18 being discrete parts. Additionally, as seen in FIG. 2, all connections to the microprocessor 12 are designated with a pin designation "RA#" or "RB#". The microprocessor 12 has the ability to connect each of the connections to an open circuit, a logical high (approximately 4.5 V), a logical low (approximately ground), a comparitor input (i.e., RA0, RA1, RA2, and RA3), and an edge detecting hardware interrupt (i.e., RB0).

In the preferred embodiment, the sensor circuit 18 of the electronic circuitry 10 includes a discharge resistor 22 which is adapted to enhance the safety of the wrist strap when worn by the user. In this respect, the discharge resistor 22 prevents a direct short to ground if the user wearing the wrist strap accidentally contacts a hot or active electrical conductor. As will be explained below, the sensor circuit 18 of the electronic circuitry 10 is adapted to perform three specific tag sensing functions. These functions include a skin resistance sensing function which is used to verify that there is a low resistance connection from the wrist strap to the user, a discharge resistance sensing function which is used to verify that the discharge resistor 22 is within a ceratin operational range, and a ground connection sensing function which continuously monitors for the connection of the wrist strap to ground.

Figure 3A:
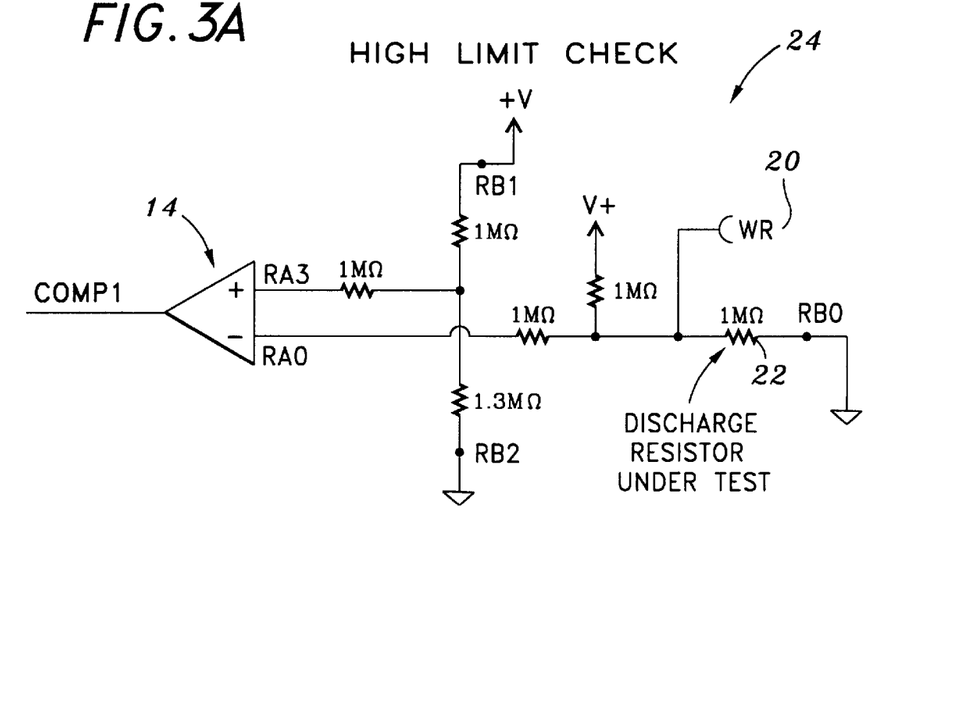
FIG. 3a is an electrical schematic of the discharge resistor check circuit of the sensor circuitry shown in FIG. 2, illustrating the high limit check sequence of the discharge resistor check circuit.
Figure 3B:
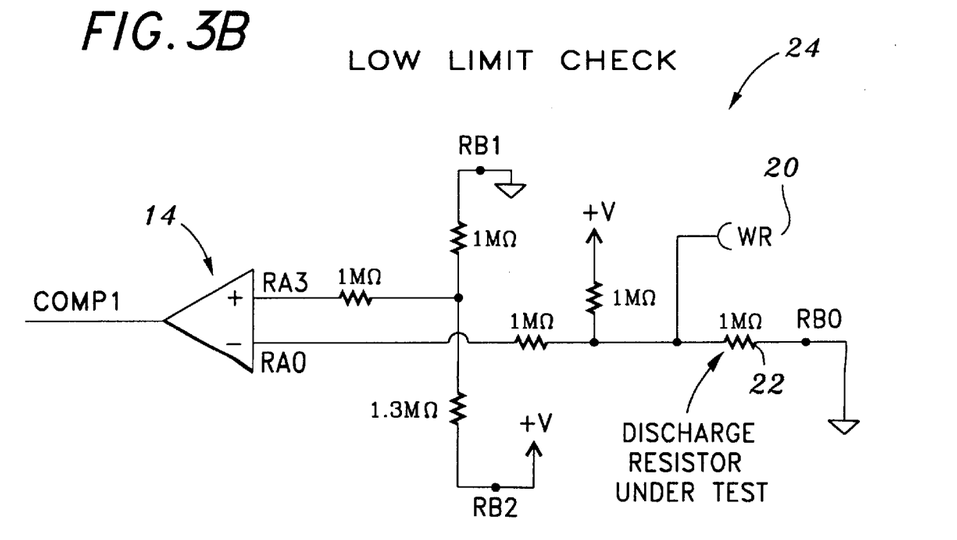
FIG. 3b is an electrical schematic of the discharge resistor check circuit of the sensor circuitry shown in FIG. 2, illustrating the low limit check sequence of the discharge resistor check circuit.

Referring now to FIGS. 3a and 3b, there is schematically illustrated a discharge resistor check circuit 24 of the sensor circuit 18 for monitoring the accuracy of the discharge resistor 22. The discharge resistor check circuit 24 is configured to perform a high limit check of the discharge resistor 22 (FIG. 3a) and a low limit check of the discharge resistor 22 (FIG. 3b). The discharge resistor 22 is checked by the discharge resistor check circuit 24 upon power up of the tag and before each transmission cycle of data from the tag to the interrogator unit. The accuracy of the discharge resistor 22 is intended to be in the range of 1 Megohm +/− 30% (i.e., 700 Kohms to 1.3 Megohms). The discharge resistor check circuit 24 is configured to generate a discharge resistor signal corresponding to the sensed accuracy of the discharge resistor 22. As will be discussed in more detail below, a discharge resistor signal which indicates a failure of the discharge resistor 22 will cause a unique fault tone to be generated by the tag. The discharge resistor signal generated by the discharge resistor check circuit 24 is transmitted to the interrogator unit during each transmission cycle of the tag.

Figure 4:
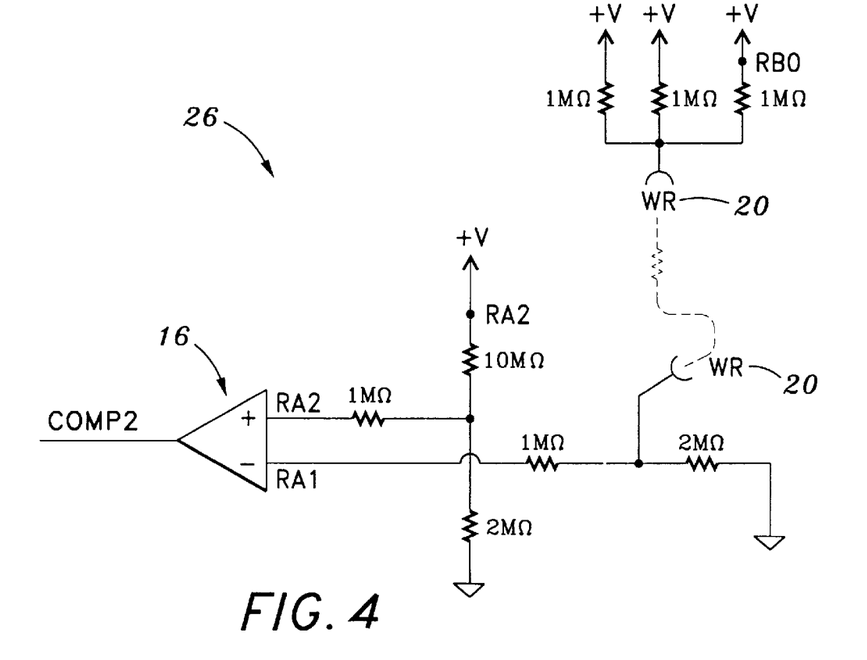
FIG. 4 is an electrical schematic of the skin resistance check circuit of the sensor circuitry shown in FIG. 2.

Referring now to FIG. 4, the sensor circuit 18 of the electronic circuitry 10 further includes a skin resistance check circuit 26 for monitoring the electrical connection of the wrist strap to the user, and more particularly the contact between the electrodes 20 and the user's skin surface. In the preferred embodiment, the user's skin resistance is tested several times by the skin resistance check circuit 26 upon the power up of the tag, and before each transmission cycle of data from the tag to the interrogator unit. The skin resistance check circuit 26 is used to verify that there is a low resistance connection (i.e., greater than 10 Megohms) from the wrist strap to the user, and more particularly between the electrodes 20 and the user's skin.

The skin resistance check circuit 26 is itself configured to generate a skin resistance signal. A skin resistance signal corresponding to at least one, and preferably several readings by the skin resistance check circuit 26 which are above 10 Megohms will trigger the generation of a unique fault tone by the tag to alert the user. The skin resistance signal generated by the skin resistance check circuit 26 is also transmitted to the interrogator unit during each transmission cycle of the tag.

Figure 5:
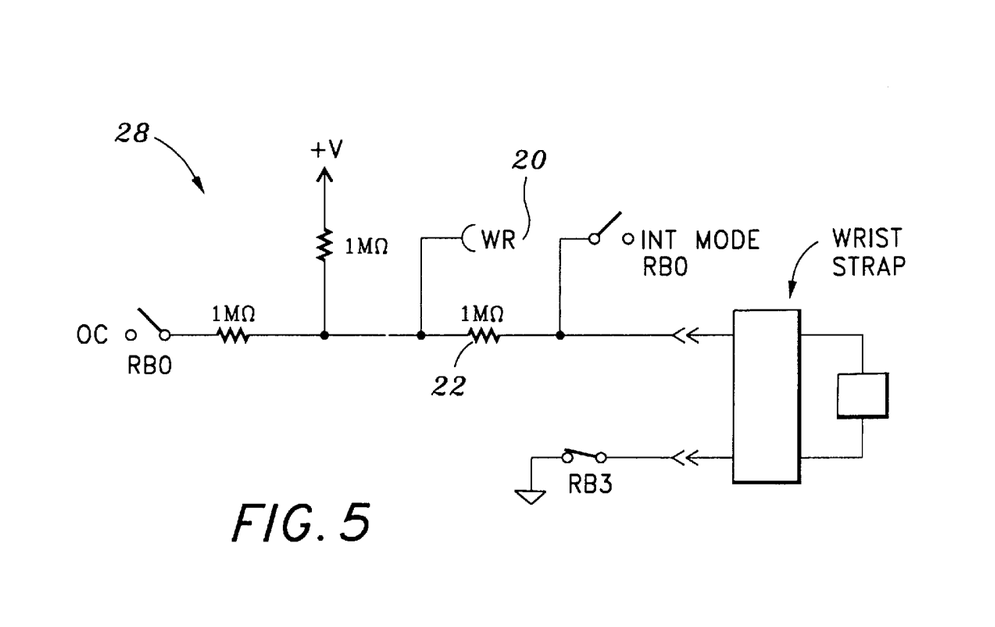
FIG. 5 is an electrical schematic of the ground fault detect circuit of the sensor circuitry shown in FIG. 2.

Referring now to FIG. 5, in addition to the discharge resistor check circuit 24 and skin resistance check circuit 26, the sensor circuit 18 of the electronic circuitry 10 includes a ground fault detect circuit 28 for monitoring the electrical connection of the wrist strap to ground. The path from the wrist strap to ground is tested upon the power up the tag, with the ground condition thereafter being continuously monitored by the ground fault detect circuit 28 which is configured to generate a ground fault signal. A ground fault signal corresponding to a passing condition for all power up tests of the tag triggers the generation of a unique tone by the tag. Additionally, a ground fault signal corresponding to a ground fault or interrupt will trigger the generation of a unique fault tone by the tag and will further immediately force the tag in a transmit mode to the interrogator unit. Otherwise, under normal operating conditions, the ground fault signal will be transmitted to the interrogator unit along with the discharge resistor and skin resistance signals during a regular data transmission cycle of the tag.

In the preferred embodiment, the electronic circuitry 10 incorporated into the tag further comprises a transmission circuit for transmitting the discharge resistor, skin resistance and ground fault signals to the interrogator unit. As previously indicated, the transmission circuit is configured to transmit the discharge resistor, skin resistance, and ground fault signals via a direct sequence spread spectrum having a data rate of approximately 33.33 kbps. All data is differentially encoded. The transmission of the discharge resistor, skin resistance, and ground fault signals by the transmission circuit to the interrogator unit preferably occurs via a carrier frequency of approximately 2414 Mhz +/− 1 Mhz.

As also previously indicated, the transmission circuit is configured to transmit the discharge resistor, skin resistance, and ground fault signals to the interrogator unit at selected transmission cycles. Each transmission cycle comprises approximately five repetitions of the signals, with each repetition being separated by a random interval of approximately three seconds. The transmission cycles preferably occur at random intervals of approximately five minutes. However, in the event an interrupt within the electrical connection of the wrist strap to ground is monitored by the ground fault detect circuit 28, the transmission circuit is configured to immediately transmit the corresponding ground fault signal to the interrogator unit. The transmission circuit may also be configured such that the discharge resistor and skin resistance signals are also immediately transmitted to the interrogator unit upon the occurrence of a change in condition of the discharge resistor 22 and/or the contact between the electrodes 20 and the user's skin.

In the preferred embodiment, the discharge resistor circuit 24 of the sensor circuit 18 is configured to periodically monitor the accuracy of the discharge resistor 22. Similarly, the skin resistance check circuit 26 is configured to periodically monitor the electrical connection of the wrist strap to the user. However, the ground fault detect circuit 28 is itself configured to continuously monitor the electrical connection of the wrist strap to ground. The accuracy of the discharge resistor 22 and the integrity of the electrical connection of the wrist strap to the user is performed when the ground is first connected, upon power up of the tag (if the ground is connected), and approximately every five minutes (corresponding to the preferred data transmission cycle of the tag).

As previously indicated, the discharge resistor, skin resistance and ground default signals are transmitted by the transmission circuit to the interrogator unit upon the power up of the tag and during each transmission cycle of the tag which preferably occurs approximately every five minutes (with a random interval). Additionally, these signals are transmitted by the transmission circuit to the interrogator unit when the ground is connected or disconnected, with the ground fault signal immediately being transmitted to the interrogator unit upon the occurrence of any interrupt within the electrical connection of the wrist strap to ground. The transmission cycles of the various signals to the interrogator unit acts as a type of confidence signal and is useful for determining the presence or absence of a tag and for determining that the tag is operating satisfactorily (e.g., that the battery is functioning properly).

The electronic circuitry 10 of the present invention further preferably comprises an alarm circuit for generating a audible alarm in response to certain conditions sensed by the discharge resistor check circuit 24, skin resistance check circuit 26, and ground fault detect circuit 28. In this respect, the alarm circuit is configured to generate an audible alarm when the accuracy of the discharge resistor 22 as monitored by the discharge resistor check circuit 24 is outside the range of approximately 1 Megohm +/− 30%. The alarm circuit is also configured to generate an audible alarm when at least one reading (and preferably several readings) of the user's skin resistance as monitored by the skin resistance check circuit 26 is above 10 Megohms. The alarm circuit is further configured to generate an audible alarm when a ground fault condition is monitored by the ground fault detect circuit 28.

Figure 6:
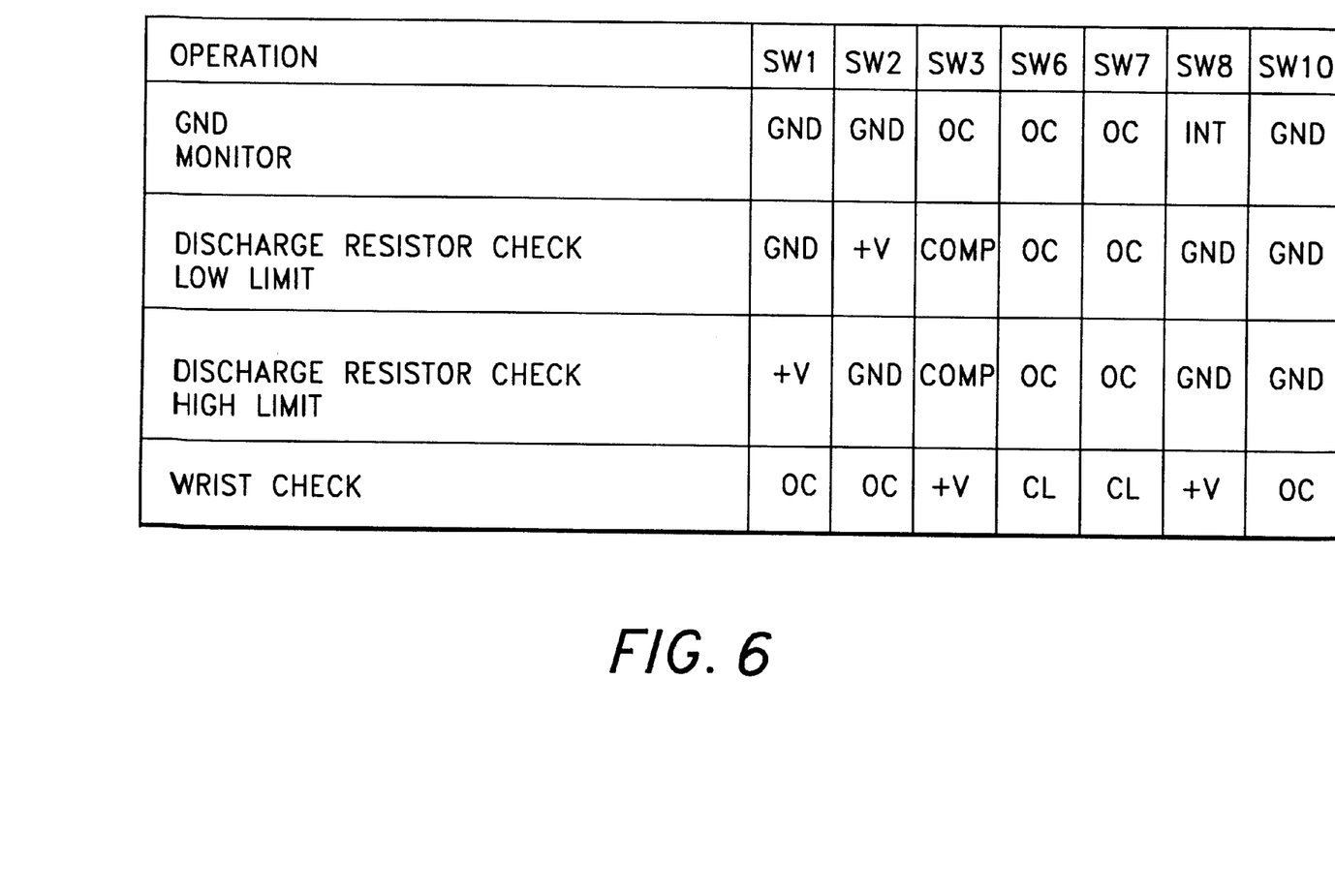
FIG. 6 is a table outlining the states that the switches and comparators of the electrical circuits shown in FIGS. 2–5 are in during the various tests conducted in the electronic circuitry of the tag constructed in accordance with the present invention.

With particular regard to the audible alarms generated by the alarm circuit of the electronic circuitry 10, a "happy tone" is generated immediately following the ground connect if the various sensor checks facilitated by the discharge resistor check circuit 24, skin resistance check circuit 26, and ground fault detect circuit 28 are within desired parameters. The "happy tone" will also be generated if the sensor checks are within the desired parameters immediately upon power up of the tag (if the ground is present). A first "sad tone" will be generated by the alarm circuit if the ground is lost, with a second sad tone being generated if the skin resistance is high. Additionally, a third sad tone will be generated if the discharge resistor 22 is high, with a fourth sad tone being generated if the discharge resistor 22 is low. The general strategy for the various audible alarms is that the user will normally only hear a "happy tone" when he/she first hooks up, and the first "sad tone" when he/she disconnects. The only time the other sad tones are heard is when a problem is sensed by the sensor circuit 18 of the electronic circuitry 10. The various states of the switches incorporated into the sensor circuit 18 during the different test phases thereof are summarized in FIG. 6.

As explained above, the tags incorporating the electronic circuitry 10 of the present invention are adapted to be able to transmit the discharge resistor, skin resistance, and ground fault signals to the interrogator unit. It is contemplated that the electronic circuitry 10 may be integrated into a universal tagging and locating system which will allow any tag to talk to any interrogator unit. Certain systems may also be provided to support encryption to allow security if needed. As also previously indicated, the tag, and more particularly the transmission circuit of the electronic circuitry 10, transmits identifying information from the tag to the interrogator unit, as well as the various signals corresponding to the status of the sensors of the tag. Additionally, data may be transmitted to the interrogator unit corresponding to the number of transmission cycles which have been executed by the tag subsequent to its activation. During a transmission of data from the tag, the interrogator unit will receive the tag signal and store the information for later processing.

Additional modifications and improvements of the present invention may also be apparent to those of ordinary skill in the art. Thus, the particular combination of parts described and illustrated herein is intended to represent only one embodiment of the present invention, and is not intended to serve as limitations of alternative devices within the spirit and scope of the invention.

What is claimed is:

1. In a static electrical discharge dissipation system having a dissipation device which is worn by a user and a conductive line for electrically connecting the dissipation device to ground, the improvement comprising a tag which electrically communicates with the dissipation device and includes electronic circuitry for monitoring the electrical connection of the dissipation device from the user to ground, the electronic circuitry of the tag comprising:

a discharge resistor;

a microprocessor having a sensor circuit which is in electrical communication with the discharge resistor and includes:

a discharge resistor check circuit for monitoring the accuracy of the discharge resistor, the discharge resistor check circuit being configured to generate a discharge resistor signal;

a skin resistance check circuit for monitoring the electrical connection of the dissipation device to the user, the skin resistance check circuit being configured to generate a skin resistance signal; and a ground fault detect circuit for monitoring the electrical connection of the dissipation device to ground, the ground fault detect circuit being configured to generate a ground fault signal;

the microprocessor being configured to multiplex the sensor circuit to facilitate the generation of the discharge resistor, skin resistance, and ground fault signals;

a transmission circuit which is in electrical communication with the sensor circuit for transmitting the discharge resistor, skin resistance, and ground fault signals to an interrogator unit.

2. The electronic circuitry of claim 1 wherein said discharge resistor check circuit is configured to perform a high limit check of the discharge resistor and a low limit check of the discharge resistor.

3. The electronic circuitry of claim 1 wherein the dissipation device comprises a static wrist strap having the tag attached thereto.

4. The electronic circuitry of claim 1 wherein the tag into which the electronic circuitry is incorporated comprises a transmit only tag.

5. The electronic circuitry of claim 1 wherein the transmission circuit is configured to transmit the discharge resistor, skin resistance, and ground fault signals via a direct sequence spread spectrum having a data rate of approximately 33.33 kbps.

6. The electronic circuitry of claim 5 wherein the discharge resistor, skin resistance, and ground fault signals are transmitted by the transmission circuit via a carrier frequency of approximately 2414 Mhz +/− 1 Mhz.

7. The electronic circuitry of claim 1 wherein the transmission circuit is configured to transmit the discharge resistor, skin resistance, and ground fault signals to the interrogator unit at selected transmission cycles.

8. The electronic circuitry of claim 7 wherein each of the transmission cycles comprises approximately five repetitions of the signals, with each repetition being separated by a random interval of approximately three seconds.

9. The electronic circuitry of claim 7 wherein the transmission circuit is configured such that the transmission cycles occur at random intervals of approximately five minutes.

10. The electronic circuitry of claim 1 wherein the transmission circuit is configured to transmit the ground fault signal to the interrogator unit immediately upon the occurrence of an interrupt within the electrical connection of the tag to ground.

11. The electronic circuitry of claim 1 wherein:
the discharge resistor check circuit is configured to periodically monitor the accuracy of the discharge resistor;
the skin resistance check circuit is configured to periodically monitor the electrical connection of the dissipation device to the user; and
the ground fault detect circuit is configured to continuously monitor the electrical connection of the dissipation device to ground.

12. The electronic circuitry of claim 1 further comprising an alarm circuit for generating an audible alarm in response to certain conditions sensed by the electronic circuitry.

13. The electronic circuitry of claim 12 wherein said alarm circuit is configured to generate an audible alarm is when the accuracy of the discharge resistor as monitored by the discharge resistor check circuit is outside the range of approximately 1 Megohm +/− 30%.

14. The electronic circuitry of claim 12 wherein said alarm circuit is configured to generate an audible alarm when at least one reading of the user's skin resistance as monitored by the skin resistance check circuit is above 10 Megohms.

15. The electronic circuitry of claim 12 wherein said alarm circuit is configured to generate an audible alarm when a ground fault condition is monitored by the ground fault detect circuit.

16. In a static electrical discharge dissipation system having a dissipation device which is worn by a user and a conductive line for electrically connecting the dissipation device to ground, a method for monitoring the electrical connection of the dissipation device from the user to ground comprising the steps of:
(a) providing a tag which electrically communicates with the dissipation device and includes electronic circuitry having a discharge resistor and a microprocessor including a sensor circuit which is in electrical communication with the discharge resistor;
(b) multiplexing the sensor circuit of the microprocessor to:
monitor the accuracy of the discharge resistor and generate a discharge resistor signal corresponding thereto via a discharge resistor check circuit of the sensor circuit;
monitor the electrical connection of the dissipation device to the user and generate a skin resistance signal corresponding thereto via a skin resistance check circuit of the sensor circuit; and
monitor the electrical connection of the dissipation device to ground and generate a ground fault signal corresponding thereto via a ground fault detect circuit of the sensor circuit;
(c) transmitting the discharge resistor, skin resistance, and ground fault signals to an interrogator unit via a transmission circuit of the electronic circuitry.

17. The method of claim 16 wherein step (b) comprises performing a high limit check of the discharge resistor and a low limit check of the discharge resistor.

18. The method of claim 16 wherein step (c) comprises transmitting the discharge resistor, skin resistance, and ground fault signals to the interrogator unit via a carrier frequency of approximately 2414 Mhz +/− 1 Mhz.

19. The method of claim 16 wherein step (c) comprises transmitting the discharge resistor, skin resistance, and ground fault signals to the interrogator unit at selected transmission cycles.

20. The method of claim 19 wherein step (c) comprises transmitting the signals at transmission cycles which each comprise approximately five repetitions of the signals, with each repetition being separated by a random interval of approximately three seconds.

21. The method of claim 19 wherein step (c) comprises transmitting the signals at transmission cycles which occur at random intervals of approximately five minutes.

22. The method of claim 16 further comprising the step of:
(d) generating an audible alarm in response to certain conditions of the electronic circuitry via an alarm circuit of the electronic circuitry.

23. The method of claim 22 wherein step (d) comprises generating an audible alarm when the accuracy of the discharge resistor as monitored by the alarm circuit is outside of the range of 1 Megohms +/− 30%.

24. The method of claim 22 wherein step (d) comprises generating an audible alarm when at least one reading of the user's skin resistance as monitored by the skin resistance check circuit is above 10 Megohms.

25. The method of claim 22 wherein step (d) comprises generating an audible alarm when a ground fault is monitored by the ground fault detect circuit.

26. The method of claim 16 wherein step (c) comprises transmitting the ground fault signal to the interrogator unit immediately upon the occurrence of an interrupt within the electrical connection of the dissipation device to ground.

27. The method of claim 16 wherein step (b) comprises:
periodically monitoring the accuracy of the discharge resistor via the discharge resistor check circuit;
periodically monitoring the electrical connection of the dissipation device to the user via the skin resistance check circuit; and
continuously monitoring the electrical connection of the dissipation device to ground via the ground fault detect circuit.

28. In a static electrical discharge dissipation system having a dissipation device which is worn by a user and a conductive line for electrically connecting the dissipation device to ground, the improvement comprising a tag which electrically communicates with the dissipation device and includes a electronic circuitry for monitoring the electrical connection of the dissipation device from the user to ground, the electronic circuitry of the tag comprising:
a discharge resistor;
a microprocessor having a sensor circuit which is in electrical communication with the discharge resistor and includes:
a discharge resistor check circuit which is operative to monitor the accuracy of the discharge resistor and generate a discharge resistor signal corresponding thereto;
a skin resistance check circuit which is operative to monitor the electrical connection of the dissipation device to the user and generate a skin resistance signal corresponding thereto; and
a ground fault detect circuit which is operative to monitor the electrical connection of the dissipation device to ground and generate a around fault signal corresponding thereto;
the microprocessor being configured to multiplex the sensor circuit to facilitate the generation of the discharge resistor, skin resistance, and ground fault signals.

29. In a static electrical discharge dissipation system having a dissipation device which is worn by a user and a conductive line for electrically connecting the dissipation device to ground, the improvement comprising a tag which electrically communicates with the dissipation device and includes electronic circuitry for monitoring the electrical connection of the dissipation device from the user to ground, the electronic circuitry of the tag comprising:

a discharge resistor; and a microprocessor having a sensor circuit which is in electrical communication with the discharge resistor;

the microprocessor being configured to multiplex the sensor circuit in a manner facilitating the generation of a discharge resistor signal corresponding to a monitored status of the accuracy of the discharge resistor, a skin resistance signal corresponding to a monitored status of the electrical connection of the dissipation device to the user, and a ground fault signal corresponding to a monitored status of the electrical connection of the dissipation device to ground.

* * * * *